(12) United States Patent
Shuma et al.

(10) Patent No.: US 11,185,379 B2
(45) Date of Patent: Nov. 30, 2021

(54) COMPREHENSIVE MESSAGING SYSTEM FOR ROBOTIC SURGICAL SYSTEMS

(71) Applicant: Verily Life Sciences LLC, South San Francisco, CA (US)

(72) Inventors: James Shuma, San Jose, CA (US); Daniel Hiranandani, Redwood City, CA (US); Joëlle Barral, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 131 days.

(21) Appl. No.: 16/244,808

(22) Filed: Jan. 10, 2019

(65) Prior Publication Data
US 2020/0222133 A1 Jul. 16, 2020

(51) Int. Cl.
*A61B 34/35* (2016.01)
*H04L 29/08* (2006.01)
*H04L 7/00* (2006.01)
*G06F 1/12* (2006.01)

(52) U.S. Cl.
CPC ............... *A61B 34/35* (2016.02); *G06F 1/12* (2013.01); *H04L 7/0008* (2013.01); *H04L 67/12* (2013.01)

(58) Field of Classification Search
CPC . G06F 1/12; G06F 1/14; H04L 7/0008; H04L 67/12; A61B 34/35; A61B 34/37
See application file for complete search history.

(56) References Cited

U.S. PATENT DOCUMENTS

| | | | | |
|---|---|---|---|---|
| 6,339,790 B1* | 1/2002 | Inoue | ...................... | H04L 41/00 709/224 |
| 6,454,708 B1* | 9/2002 | Ferguson | ............... | G16H 10/65 600/300 |
| 6,760,337 B1* | 7/2004 | Snyder, II | ........... | H04L 12/5602 370/395.4 |
| 7,697,558 B2* | 4/2010 | Pilon | .................... | H04M 11/062 370/430 |
| 8,943,168 B2* | 1/2015 | Wiesner | ............... | A61B 5/0026 709/217 |

(Continued)

OTHER PUBLICATIONS

Taylor et al., "Computer-integrated surgery and medical robotics", Standard Handbook of Biomedical Engineering and Design (2002): 325-353.

(Continued)

*Primary Examiner* — Nam T Tran
(74) *Attorney, Agent, or Firm* — Kilpatrick Townsend & Stockton LLP

(57) ABSTRACT

One example method for comprehensively recording and reporting messages generated within a robotic surgical system includes capturing and storing network data on an internal network of the robotic surgical system. The method further includes subscribing to and receiving published messages from processes of interest executing on one or more task devices of the robotic surgical system. The received published messages each is associated with a priority. The method further involves sending at least a portion of the published messages according to the respective message priorities to a server device for analysis. Based on the analysis result, the method involves causing the surgical robotic system to be modified to improve its performance.

20 Claims, 5 Drawing Sheets

(56) References Cited

U.S. PATENT DOCUMENTS

| | | | |
|---|---|---|---|
| 8,977,336 B2* | 3/2015 | Huennekens | A61B 5/0084 |
| | | | 600/407 |
| 9,832,135 B2* | 11/2017 | Robertson | H04L 47/6295 |
| 10,242,159 B2* | 3/2019 | Kamen | G16H 20/17 |
| 10,500,728 B2* | 12/2019 | Asano | B25J 9/1689 |
| 10,506,084 B2* | 12/2019 | Pal | H04L 69/329 |
| 2004/0172222 A1* | 9/2004 | Simpson | G08B 21/02 |
| | | | 702/189 |
| 2007/0150631 A1* | 6/2007 | Druke | B25J 9/1661 |
| | | | 710/244 |
| 2007/0230361 A1* | 10/2007 | Choudhury | H04L 41/5038 |
| | | | 370/250 |
| 2009/0036750 A1* | 2/2009 | Weinstein | G16H 40/20 |
| | | | 600/300 |
| 2009/0248043 A1 | 10/2009 | Tierney et al. | |
| 2011/0275907 A1 | 11/2011 | Inciardi et al. | |
| 2012/0185267 A1 | 7/2012 | Kamen et al. | |
| 2012/0197911 A1* | 8/2012 | Banka | G06F 16/951 |
| | | | 707/752 |
| 2013/0023762 A1 | 1/2013 | Huennekens et al. | |
| 2013/0191154 A1* | 7/2013 | William R. | G06F 3/0482 |
| | | | 705/3 |
| 2014/0051984 A1 | 2/2014 | Berger et al. | |
| 2014/0207286 A1 | 7/2014 | Wang et al. | |
| 2014/0288412 A1 | 9/2014 | Schwartz | |
| 2016/0105275 A1 | 4/2016 | Thomas et al. | |
| 2017/0235880 A1 | 8/2017 | Wright et al. | |
| 2018/0122506 A1* | 5/2018 | Grantcharov | G06F 17/40 |
| 2019/0005838 A1 | 1/2019 | Yu et al. | |
| 2019/0199599 A1* | 6/2019 | Zavesky | H04L 41/16 |
| 2019/0206562 A1* | 7/2019 | Shelton, IV | B25J 13/006 |
| 2020/0145492 A1* | 5/2020 | Slik | H04L 67/2852 |

OTHER PUBLICATIONS

PCT/US2019/066659, "International Search Report and Written Opinion", dated Feb. 26, 2020, 8 pages.

* cited by examiner

COMPREHENSIVE MESSAGING SYSTEM FOR ROBOTIC SURGICAL SYSTEMS

FIELD

The present application generally relates to robotic surgery and message reporting, and more particularly relates to comprehensively recording and reporting messages associated with a robotic surgical system.

BACKGROUND

The use of robotic surgical systems to assist with surgical procedures is becoming increasingly common. Robotic surgical systems may assist with any aspect of surgery, including but not limited to insertion or removal of surgical instruments, resection of tissue, insertion of implanted devices, etc. Robotic surgical systems, however, are highly complicated systems involving interactions among various components and devices. A large amount of messages or data are generated in the robotic surgical systems during robotic surgical procedures. These messages or data are valuable to assist in tasks such as engineering the system, analyzing fleet-wide usage, monitoring fleet health, automatically initiating service calls, tracking usage of disposable surgical tools, and thoroughly investigating incidents.

SUMMARY

Various examples are described for comprehensively recording and reporting messages generated within a robotic surgical system. One example method includes synchronizing clocks associated with a plurality of computing devices in a robotic surgical system through a time synchronization protocol implemented by each of the plurality of computing devices, wherein the plurality of computing devices are connected through an internal network of the robotic surgical system; capturing, by a first computing device of the plurality of computing devices, network data sent over the internal network of the robotic surgical system by the plurality of computing devices, wherein the network data are associated with timestamps generated based on the respective clocks of the plurality of computing devices; storing, by the first computing device, the network data in a storage device associated with the first computing device based on the timestamps associated with the network data for a pre-determined period of time; receiving, by the first computing device through the internal network, a set of published messages published by at least a second computing device through one or more dedicated network ports, each of the set of published messages associated with a message priority and a timestamp generated based on the clock of the second computing device, wherein the network data captured by the first computing device over the internal network contain the set of published messages; transmitting, by the first computing device over an external network, at least a portion of the set of published messages to a server device for processing according to the respective message priorities and timestamps; receiving, within the pre-determined period of time, a request to retrieve the network data, wherein the request is generated based on the portion of the set of published messages transmitted to the server device and specifies one or more criteria for retrieving the network data; retrieving the network data that satisfy the one or more criteria; and transmitting, by the first computing device over the external network, the retrieved network data to the server device in response to the request.

One example system includes a plurality of task devices connected via an internal network, wherein one or more processes execute on the plurality of task devices, and wherein each of the plurality of task devices are configured to implement a time synchronization protocol for synchronizing clocks associated with the plurality of computing devices; and a messaging device connected with the plurality of task devices via the internal network. The messaging device includes a processor and a non-transitory computer-readable medium having processor-executable instructions stored thereupon, which, when executed by the processor, cause the processor to synchronize a clock associated with the messaging device with the clocks of the plurality of task devices through implementing the time synchronization protocol; capture network data sent over the internal network by the plurality of task devices, wherein the network data are associated with timestamps generated based on the respective clocks of the plurality of task devices; store the network data in a storage device associated with the messaging device based on the timestamps associated with the network data for a pre-determined period of time; receive a set of published messages published by the one or more processes, each of the set of published messages associated with a message priority and a timestamp generated based on the clock of a corresponding task device, wherein the network data captured by the messaging device over the internal network contains the set of published messages; transmit, over an external network, at least a portion of the set of published messages to a server device for processing according to the respective message priorities and timestamps; receive, within the pre-determined period of time, a request to retrieve the network data, wherein the request is generated based on the portion of the set of published messages transmitted to the server device and specifies one or more criteria for retrieving the network data; retrieve the network data that satisfy the one or more criteria; and transmit, over the external network, the retrieved network data to the server device in response to the request.

One example computing device includes a processor and a non-transitory computer-readable medium having processor-executable instructions stored thereupon, which, when executed by the processor, cause the processor to: synchronize clocks associated with a plurality of task devices in a robotic surgical system through implementing a time synchronization protocol, wherein the computing device and the plurality of task devices are connected through an internal network of the robotic surgical system; capture network data sent over the internal network by the plurality of task devices, wherein the network data are associated with timestamps generated based on the respective clocks of the plurality of task devices; store the network data in a storage device associated with the computing device based on the timestamps associated with the network data for a pre-determined period of time; receive a set of published messages published by at least one of the task devices, each of the set of published messages associated with a message priority and a timestamp generated based on the clock of a corresponding task device, wherein the network data captured by the messaging device over the internal network contain the set of published messages; transmit, over an external network, at least a portion of the set of published messages to a server device for processing according to the respective message priorities and timestamps; receive, within the pre-determined period of time, a request to retrieve the network data, wherein the request is generated based on the portion of the set of published messages transmitted to the server device and specifies one or more criteria for retrieving the network data; retrieve the network data that satisfy the one or more criteria; and transmit, over the external network, the retrieved network data to the server device in response to the request.

One example non-transitory computer-readable medium comprising processor-executable instructions to cause a processor to: synchronize a clock associated with the processor with clocks associated with a plurality of task devices in a robotic surgical system through implementing a time synchronization protocol, wherein a computing device containing the processor and the plurality of task devices are connected through an internal network of the robotic surgical system; capture network data sent over the internal network by the plurality of task devices, wherein the network data are associated with timestamps generated based on the respective clocks of the plurality of task devices; store the network data in a storage device associated with the computing device based on the timestamps associated with the network data for a pre-determined period of time; receive a set of published messages published by at least one of the task devices, each of the set of published messages associated with a message priority and a timestamp generated based on the clock of a corresponding task device, wherein the network data contain the set of published messages; transmit, over an external network, at least a portion of the set of published messages to a server device for processing according to the respective message priorities and timestamps; receive, within the pre-determined period of time, a request to retrieve the network data, wherein the request is generated based on the portion of the set of published messages transmitted to the server device and specifies one or more criteria for retrieving the network data; retrieve the network data that satisfy the one or more criteria; and transmit, over the external network, the retrieved network data to the server device in response to the request.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
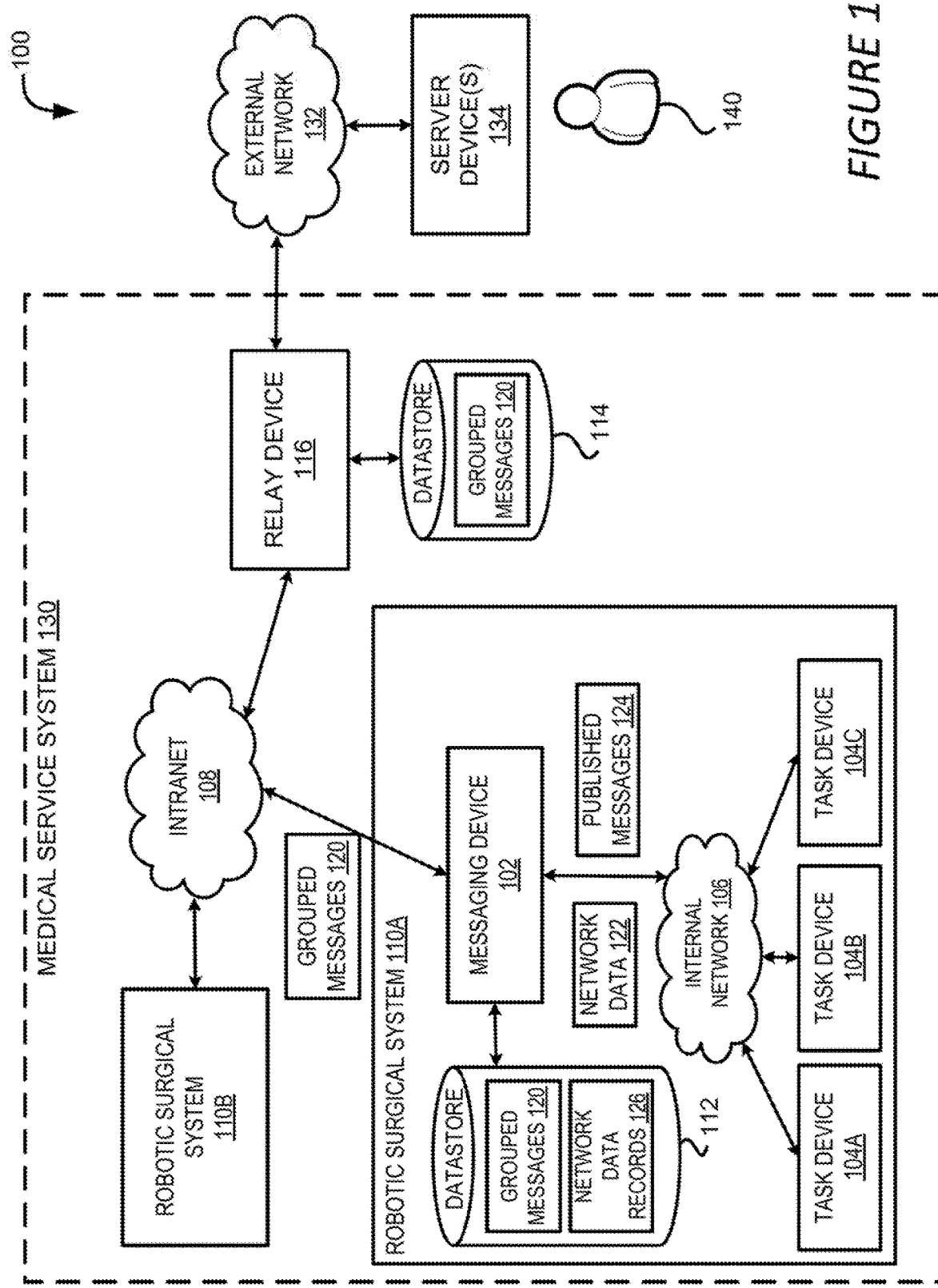
FIG. 1 shows an example of a computing environment where various messages generated within robot surgical systems of a medical service system are comprehensively recorded and reported.

Examples are described herein in the context of comprehensively recording and reporting messages generated within a robotic surgical system. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example of comprehensively recording and reporting messages generated within a robotic surgical system, the robotic surgical system employs a messaging device to monitor and record messages generated by task devices of the robotic surgical system. The task devices execute various processes to perform tasks related to robotic surgeries, such as receiving and processing commands from a surgeon, transmitting the commands to the robots, controlling robots to perform surgeries based on the commands of the surgeon, and so on. The messaging device includes a data trace recorder for monitoring and recording network data sent by the task devices over an internal network of the robotic surgical system during a robotic surgical procedure. In this example, the data trace recorder records all the data sent over the internal network, and stores them as network data records in a secure data store.

The messaging device also includes a message reporting service for receiving published messages from various processes executing on the task devices. Generally, these messages are deemed important and thus are actively published by the processes of the task devices, and may include information such as faults or events detected by the task device, in contrast to ordinary network traffic which is typically not transmitted by the task devices for the express purpose of logging or notification. The message reporting service organizes the received published messages into groups based on their associated priorities and transmits the grouped messages according to their priorities to a server device. For example, messages indicating a patient injury or a malfunction of a surgical tool are typically assigned a higher priority by the process executing on the task device and transmitted before other low-priority messages such as debugging messages so that high-priority messages can be received by the server device first.

The server device performs analysis utilizing the received grouped messages to, for example, generate or cause to be generated feedback to the robotic surgical system, such as an instruction or notification to replace a malfunctioning robotic tool, an instruction to cease the surgical procedure or cease using the robot itself to avoid further patient injury, a change to the configuration of robotic arms to improve the performance of the system, or a change to the setting of the robotic surgical system to eliminate an error that occurred in the system. In one example, the feedback is provided in real time or near real time to the robotic surgical system so that the system is modified immediately to avoid future damages, such as patient injury or a system failure.

Based on the received grouped messages, a user of the server device, such as a system administrator, a service team, support staff, or an engineer, may further request additional data related to the received grouped messages. In response to the request, the messaging device queries the secure data store to retrieve network data records relevant to, but more comprehensive than, the grouped messages and uploads those network data records to the server device for further analysis. By comprehensively storing all of the network traffic and published messages during the course of a surgical procedure, the messaging device is able to supply a much richer set of data that can enable after-the-fact diagnosis of issues and troubleshooting. Further, by only selectively forwarding some of the recorded data to the remote server, limited bandwidth between the robotic surgical system and the remote server can be conserved for information that is truly needed at the server. But because the volume of data generated during a single surgical procedure, it may only be stored for a limited time. Thus, the network data records are deleted periodically to release storage spaces for new network data records.

The technology presented herein improves the robotic surgical system by comprehensively recording and reporting messages of the robotic surgical system which are analyzed to improve the performance of the system. Comprehensively monitoring and recording these messages and data is challenging because there are multiple devices individually operating within the system, and correctly recording the relative ordering of events across the system is nontrivial. The task is further complicated by the fact that the robotic surgical system generates information requiring logging at an extremely high rate and thus recording the information also need to be performed timely and efficiently. In addition, the large volume of data further imposes a challenge on the computing resources of the system, including the consumption of CPU time, memory space and network bandwidth.

The technology presented herein solves the above problem by comprehensively recording data of the robotic surgical system even if the data are not foreseen to be useful at the time of recording, and storing these data for a certain period of time so that the data are available if needed after the fact, such as to diagnose problems with the robotic surgical system and to enable more effective troubleshooting. Without comprehensively recording the network data, critical information might be lost because the information was not previously foreseen as being useful.

In the meanwhile, published messages are captured, processed and transmitted based their respective priorities. Compared with the network data records, the published messages have a much smaller size and thus require less network bandwidth for transmission. By processing only the published messages rather than the entire network data records, the resource consumption of the message device 102, such as the processing resource (i.e. CPU) consumption and network resource consumption, is reduced whereas the comprehensive network data records are maintained for future retrieval if requested. Further, by transmitting the messages with the highest priority first, the latency in transmitting the messages of interest are reduced. In addition, message recording and reporting can also improve the safety of the robotic surgery system by providing high-priority messages in real time or near real time to the server device for analysis so that abnormal events or activities associated with the robotic surgical system can be detected and terminated. Other technical advantages other than those mentioned herein can also be realized from implementations of the technologies disclosed herein.

This illustrative example is given to introduce the reader to the general subject matter discussed herein and the disclosure is not limited to this example. The following sections describe various additional non-limiting and non-exhaustive examples of comprehensively recording and reporting messages generated within a robotic surgical system.

Referring now to FIG. 1, FIG. 1 shows an example of a computing environment 100 where messages generated within robot surgical systems of a medical service system are comprehensively recorded and reported to a server device for analysis. The example computing environment 100 includes a medical service system 130, such as a hospital computing system, where one or more robotic surgical systems 110A-110B (which may be referred to herein individually as a robotic surgical system 110 or collectively as the robotic surgical systems 110) are employed to perform various surgeries. In one example, the robotic surgical systems 110 are connected through a network, such as an intranet 108 which is accessible to devices and systems within the medical service system 130.

In the example shown in FIG. 1, a robotic surgical system 110 includes multiple task devices 104A-104C, which may be referred to herein individually as a task device 104 or collectively as the task devices 104, that are configured to perform various tasks associated with the robotic surgical system 100 or robotic surgeries performed using the robotic surgical system 110. For example, a task device 104A might be configured to provide an user interface to a surgeon to receive commands from the surgeon, process and transmit the commands to a surgical robot (not shown in FIG. 1) of the robotic surgical system 110. Another task device 104B might be configured to receive and process the commands sent from the task device 104A and to control the surgical robot accordingly. Yet another task device 104C might be configured to coordinate the components of the robotic surgical system 110 to ensure consistencies in input and output data of the system. As shown in FIG. 1, these task devices 104 communicate with each other via an internal network of the robotic surgical system 110, such as an Ethernet or a wireless network. Further, it should be appreciated that a robotic surgical system according to this disclosure may have any suitable number of task devices 140, and is not limited to the three shown, or required to have at least three.

The example robotic surgical system 110 shown in FIG. 1 also includes a messaging device 102 configured to record and report messages in the robotic surgical system 110. The messaging device 102 is also connected to the internal network 106 and communicates with the task devices 104 through the internal network 106. The messaging device 102 is also connected to an external network, such as the external network 132, via an intranet 108 of the medical service system 130 so that the messaging device 102 can transmit recorded messages outside the internal network 106. The messaging device 102 may be a personal computer ("PC"), a desktop workstation, a laptop, a server computer, or any other computing device capable of connecting to the internal network 106 and communicating with the task devices 104.

In one example, the messaging device 102 subscribes to and receives published messages 124 from the task devices 104. For instance, the messaging device 102 maintains a configuration file containing the published messages 124 that will be published by the task devices 104 and monitors these task devices for the published messages 124. These messages generally includes messages such as error messages, event messages, or warning messages related to the robotic surgical system 110 that the task devices 104 are configured to generate and publish to the rest of the robotic surgical system. The messaging device 102 organizes the published messages 124 into grouped messages 120, for example, based on priorities of the messages assigned by respective task devices 104, and stores the grouped messages 120 in a datastore 112.

Because the published messages are pre-determined, such as by the developers or engineers of the processes executing on the task devices 104, these messages might not provide all the information required to perform an analysis or an investigation of an event occurred in the robotic surgical system 110. The messaging device 102 is thus also configured to monitor and capture network data 122 sent over the internal network 106 and record the network data 122 as network data records 126 in the datastore 112. In one example, the messaging device 102 captures and records substantially all the network data 122 observed on the internal network 106, including the published messages 124, so that these comprehensive data can be retrieved for analysis when needed. Detailed examples of recording the network data 122 and the published messages 124 will be provided with respect to FIG. 2.

The datastore 112 can be a physical storage device or a virtualized storage device. In one example, the datastore 112 includes a redundant array of independent disks ("RAID") storage that combines multiple physical disk drive components into one or more logical units for the purposes of data redundancy, performance improvement, or both. Other storage devices or technologies can also be utilized here. Considering that the grouped messages 120 and the network data records 126 contain a large amount of data, the messaging device 102 stores the grouped messages 120 and the network data records 126 on the datastore 112 for a certain period of time, referred to herein as a storage time period, such as two weeks or a month. Upon expiration of the storage time period, the messaging device 102 deletes the grouped messages 120 and the network data records 126 to provide storage space for newly recorded data. Detailed examples of storing the grouped messages 120 and the network data records 126 are provided herein with respect to FIGS. 3A and 3B.

To facilitate the analysis of the robotic surgical system 110, the messaging device 102 further uploads or otherwise transmits the grouped messages 120 to a server device 134. The server device 134 may represent one or more conventional server computers, Web servers, cloud servers, database servers, or network appliances. Alternatively, the server device 134 may represent a user computing device, such as a PC, a desktop workstation, a laptop, a notebook, a mobile device, and the like. It will be appreciated that the server device 134 may represent any server computers or user computing devices known in the art.

In one example, the server devices 134 host an online service to provide a message repository and a message analysis platform. A user 140 of the online service may utilize the online service to view the messages recorded for different robotic surgical systems 110 in different medical service systems 130, perform analysis on the recorded messages, request additional messages from corresponding messaging devices 102, or send feedback or instructions to the robotic surgical system 110. For example, the user 140 can analyze the received messages or data and determine the part of the robotic surgical system 110 that is frequently in fault, determine how the operators or surgeons used the surgical tools to detect misuse of the surgical tools, or track the status of different parts of the surgical robot, such as the temperature of a robotic arm to identify the parts that are in faulty condition. The user 140 can be a surgeon and a nurse who operated the robotic surgical system 110, an administrator to control site policy, such as policies on recording the messages, or service personnel responsible for maintaining the robotic surgical system 110.

Based on the analysis, the server device 134 sends a feedback message to the robotic surgical system 110, such as an instruction to cease the surgery procedure to avoid further patient injury, or a change to the configuration of the robotic surgical system to eliminate an error occurred in the system. In one example, the feedback is provided in real time or near real time to the robotic surgical system 110 so that the system is modified immediately to avoid future damages, such as patient injury or a system failure. Based on the analysis, the server device 134 can also send a message to service personnel so that a change to the configuration of robotic arms can be made to improve the performance of the system.

In some implementations, due to security reasons and other considerations, the robotic surgical system 110 has a limited period of time in which it is connected to an external network, also referred to herein as a "connection window." For instance, the messaging device 102 might be configured to connect to the external network based on a configuration file indicating a connection window of 20 minutes for every 30 minutes. In these implementations, the recorded data, such as the grouped messages 120, might not be uploaded completely to the server device 134 within the connection window due to the large volume of data and the limited network speed when connecting to the external network 132.

To mitigate the problem, instead of directly transmitting the grouped messages 120 to the server devices 134, the messaging device 102 uploads the recorded data to a relay device 116 of the medical service system 130. The relay device 116 can be a gateway, a hub, a server computer, or any other computing device capable of connecting to the intranet 108 to communicate with the messaging device 102 and connecting to the external network 132 to communicate with the server devices 134. Because the messaging device 102 and the relay device 116 are located within the same intranet 108, the uploading speed is generally faster than the external network 132 and the messaging device 102 is more likely to finish the uploading within the connection window.

In this way, the relay device 116 is used as a buffer to receive the data to be uploaded from the messaging device 102. The relay device 106 stores the received grouped messages 120 in a datastore 114 and then uploads the grouped messages 120 to the server devices 134 at a speed suitable for the external network 132. In some implementations, the connection between the relay device 106 and the server device 134 is an encrypted connection using, for example, transport layer security ("TLS") to ensure that the data are securely transmitted to the server device 134.

In another implementation, the medical service system 130 prohibits the robotic surgical systems 110 from connecting to the external network 132. In those scenarios, the messaging device 102 can similarly upload the grouped messages 120 to a relay device 116 of the medical service system 130 that is permitted to have a connection to the external network 132. The relay device 116 then uploads the grouped messages 120 to the server devices 134 through the external network 132. In yet another implementation, the messaging device 102 uploads the grouped messages 120 to the relay device 116 regardless of the existence of the connection window or whether it is prohibited from connecting to the external network 132.

Figure 2:
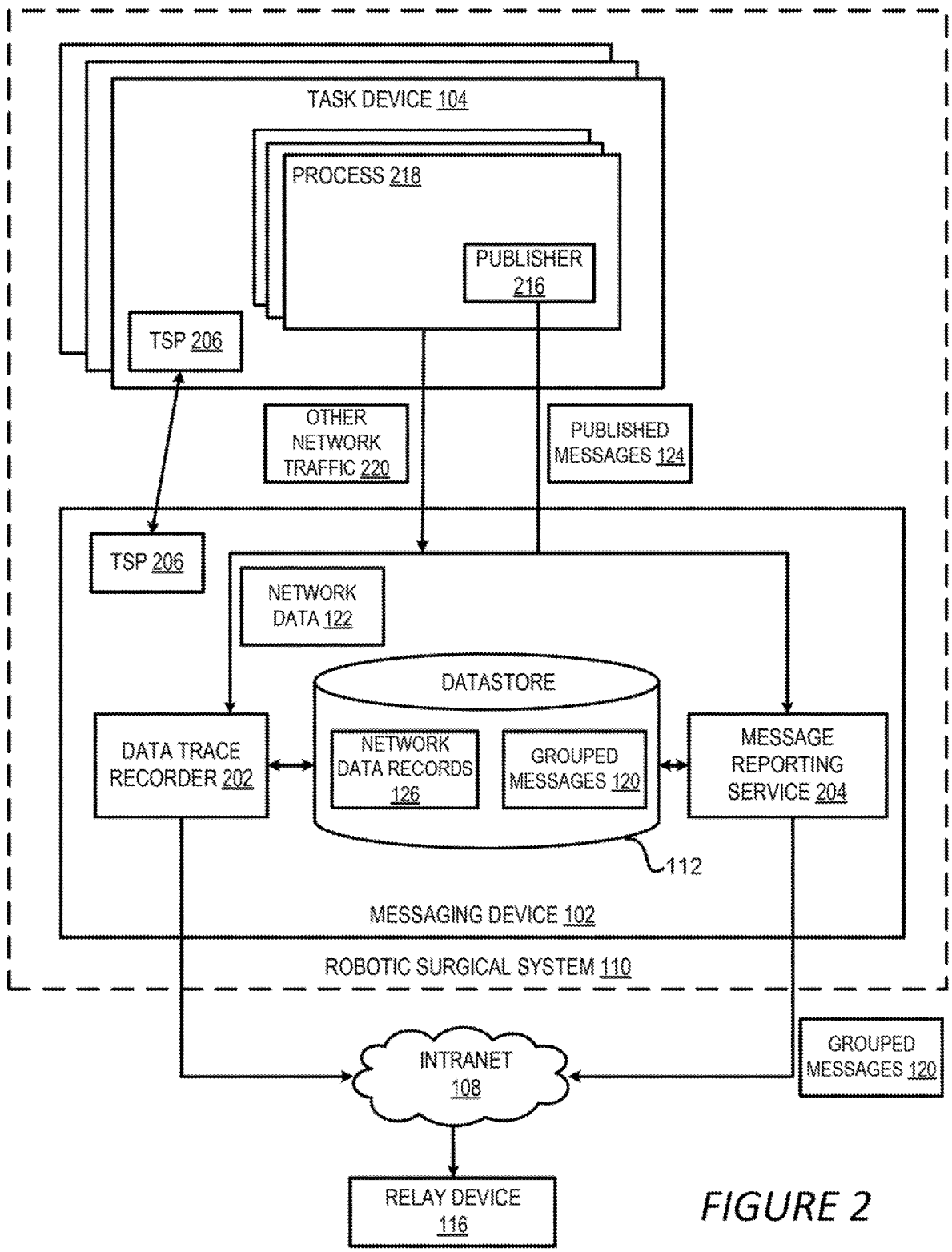
FIG. 2 shows a block diagram illustrating an example of a robotic surgical system where messages are comprehensively recorded and reported.

FIG. 2 shows a block diagram illustrating an example of a robotic surgical system 110 where messages are comprehensively recorded and reported. As shown in FIG. 2, each of the task devices 104 includes one or more processes 218. For example, a task device 104 can include a process for presenting a user interface to a surgeon and receiving the surgeon's input. The task device 104 can further include a process for processing the surgeon's input to determine whether the surgeon has input a command for controlling a robotic arm of a surgical robot, to convert the command to a format that is acceptable by the surgical robot, and to send the command to the surgical robot. The task device 104 can also include a process for transmitting the converted command to another task device 104 associated with the surgical robot. Similarly, the other task device 104 can include various processes for completing the tasks that the other task device 104 is configured to perform.

These processes 218, or at least some of them, each include a publisher 216. The publisher 216 is a component of the process 218 that collects pre-defined messages generated during the execution of the process 218 and broadcasts, i.e. publishes, the messages over the internal network 106 as published messages 124. The published messages 124 can include, in terms of severity of the messages for example, error messages, warning messages, debug information generated while executing the process 218, and status information of the process 218 collected at various stages of the process 218.

According to some aspects, the publisher 216 also assigns different priorities to the published messages 124. By default, the severity of the messages indicates their priorities, that is, error messages are assigned the highest priority, warning messages are assigned the second highest priority and so on. This default assignment of priorities can be overwritten by assigning a priority to a message regardless of its severity. For example, messages related to a patient injury, whether they are error messages, warning messages, status information or debug information, may need to be uploaded to the server device 134 immediately and thus may be assigned a highest priority. On the other hand, routine messages related to regular maintenance of the robotic surgical system 110, even if they are error messages, can be assigned a lower priority. Messages that are deemed to be non-urgent or unimportant are categorized as deferred messages and assigned an even lower priority, such as messages related to fine-grained user input tracking. Any other messages may be assigned the lowest priority.

In one example, the process 218 broadcasts the published messages 124 on different ports. For published messages 124 that have four different priorities, the process 218 employs four different ports, each port for one priority, to broadcast the published messages 124. In other words, published messages 124 having the first priority are broadcast or published on the first port; published messages 124 having the second priority are broadcast or published on the second port, and so on. For other network traffic 220, i.e. network data other than the published messages 124, the process 218 transmits as usual without broadcasting on a dedicated port.

To receive the published messages 124, the messaging device 102 employs a message reporting service 204. The message reporting service 204 subscribes to, for example through a logging subscriber, the published messages 124 of processes of interest. The processes of interest include those processes 218 from which the server device 134 is interested in receiving. For example, the server device 134 is interested in receiving published messages 124 containing operational status of a surgical robot from a process configured for monitoring the status of the surgical robot, but is less interested in receiving published messages by a process configured to generate a user interface for presenting data. In this example, the logging subscriber subscribes to the published messages 124 from the first process, but not the latter one.

The message reporting service 204 listens to the ports assigned to the different priorities of subscribed published messages to capture the published messages 124 and writes these messages to the datastore 112. Based on the port from which a published message 124 is received, the message reporting service 204 can determine the priority of the published message 124. In another example, the priority of the published messages 124 is also included in the message itself. Based on the priorities of the published messages 124, the message reporting service 204 organizes the published messages 124 into grouped messages 120. Detailed examples of generating and storing the grouped messages 120 are provided herein with respect to FIG. 3A.

It should be understood that while four priorities are described in the above example, any number of priorities can be utilized to categorize the published messages and any number of ports can be used to publish the messages. Further, messages in different priority categories can be published on the same port and messages in the same priority category might be published through different ports. In addition, the published messages 124 can each contain a priority associated with the respective messages, and as a result, the priority of a message can be determined based on the port where it is published or based on the priority contained in the message itself. It should be further understood that the message reporting service 204 can also receive published message from devices external to the robotic surgical system, such as other devices in the same operating room as the robotic surgical system, or another device in the medical service system 130.

In one example, the message reporting service 204 is also configured to detect and tag a grouped message 120 as containing sensitive information, such as protected health information ("PHI"). For example, the message reporting service 204 can tag or label fields of the message that might contain sensitive information such as a field containing patient names. These fields can be pre-defined as containing sensitive data and be recognized by the message reporting service 204. In other scenarios where the messages do not include structured fields, the message reporting service 204 can detect the sensitive information by recognizing characteristic identifiers such as "#phi." These characteristic identifiers can be inserted by the processes 218 when generating published messages to indicate the sensitive nature of that portion of the message. In some aspects, the message reporting service 204 can employ a machine learning tool to automatically detect sensitive information in the grouped messages 120, such as a machine learning model trained with sensitive data. Various other mechanisms can be utilized to detect the sensitive data. In some implementations, once the portion of the message is tagged or classified as containing sensitive data, that tag or classification will be retained for the lifetime of the data.

Upon detecting the sensitive information, the message reporting service 204 further de-identifies the grouped messages 120 to ensure that no sensitive information is transmitted to the server device 134 if the permission for uploading such information has not been obtained or if the medical service system 130 is located in a jurisdiction where such uploading is prohibited. The sensitive data can be de-identified by removing the sensitive data or removing the fields containing the sensitive data. Depending on the applicable sensitive data policy, the de-identification can be performed by the messaging device 102 or the relay device 116 if the policy requires no sensitive data to be released outside the intranet 108. The de-identification can be even performed at the server device 134 if the policy only prohibits disclosing the sensitive data to a third party.

In some implementations, the message reporting service 204 can identify the sensitive data and perform the de-identification prior to storing the grouped messages 120 into the datastore 112. Alternatively, or additionally, the message reporting service 204 can generate a de-identified version of the grouped messages 120 for upload in addition to the original grouped messages 120.

The message reporting service 204 further compresses the grouped messages 120 using Gzip, Zip, or any other file compression mechanisms known in the art, such as video compression mechanism for compressing messages including video. The compression can be performed to reduce the size of the messages by a fixed amount (e.g. reduce by 50%) or to a given size (e.g. 5 GB). In some aspects, the compression can be performed based on factors such as the available bandwidth, the time to upload the message, the compressibility of the messages and so on. For example, if a message is received in a compressed form, the compressibility of the message is low and it would be less beneficial to further compress the message. Further, if the available network bandwidth is low, the message should be compressed using a higher compression ratio. Likewise, if the time to upload the message is long, then it is beneficial to compress the message more to reduce the upload time. Various other factors can be considered when determining whether and how to compress the messages before the upload. The compressed grouped messages 120 are then transmitted in the order of their respective priorities, that is, a grouped message 120 having a higher priority is transmitted before a grouped message 120 having a lower priority. The grouped messages 120 can be transmitted directly, or through the relay device 116, to the server device 134 over the external network 132 as discussed above with respect to FIG. 1. In some implementations, grouped messages 120 having the lowest priority are not uploaded to the server device 134.

As discussed above, recording and reporting the grouped messages 120 requires the user 140 or other individuals, such as the engineer of the robotic surgical system 110, to foresee the type of messages that he or she wants the system to record. In some cases, however, those messages cannot provide enough information to perform the analysis. For example, in an incident investigation, the recorded messages containing a faulty status of the surgical robot may not provide information regarding how the surgical robot arrived at such a faulty status, and what caused the fault. Even if the user 140 had foreseen that this additional information would be useful and had these information recorded, there are still scenarios where unexpected fault occurs and unforeseen, but critical, data are needed to perform the analysis or investigation. It is thus beneficial to record as much data as possible even though not all data are useful and need to be transmitted to the server device 134 for a given analysis.

To achieve such a goal, the messaging device 102 in the example shown in FIG. 2 employs a data trace recorder 202. The data trace recorder 202 is configured to capture all the network traffic on the internal network 106 of the robotic surgical system 110. For example, the data trace recorder 202 implements a network sniffer using network packet sniffing and crafting libraries such as the libtins and libpcap libraries. In addition, the network interface controller of the messaging device 102 is placed in promiscuous mode so that the controller passes all traffic it receives to the central processing unit (CPU) rather than passing only the frames that the controller is specifically programmed to receive.

The messaging device 102 then stores the captured network data 120 on the datastore 112 as network data records 126. An example of the network data records 126 will be described below with respect to FIG. 3B. Because the network data 122 contains all the network traffic on the internal network 106, the size of the network data 122 and the network data records 126 is significantly larger than the grouped messages 120. If the network data records 126, or a portion thereof, are to be uploaded to the server device 134, the network bandwidth consumption would be significantly higher than that when uploading the grouped messages 120.

To reduce the size of the network data records 126 to be uploaded, the data trace recorder 202 can optionally implementing a filtering process to delete certainly type of network data, for example, data irrelevant to the operation of the surgical robot, such as the network request message, acknowledgement or negative-acknowledgement packets. The filtering process can also reduce the fidelity of the network data records 126 that are retained on the datastore 112 before transmission. For example, the robotic surgical system 110 might be configured to record the temperature of a robotic arm several times per second and communicate such temperature measurements to a controlling task device. Instead of uploading or transmitting all the temperature measurements within a second, the filtering process can down sample the temperature data, such as retaining every other temperature measurement for the robotic arm. In another example, robot motion captured at several kHz can be filtered to reduce the frequency to, for example, 60 Hz to reduce the network bandwidth consumption.

In one example, the messaging device 102 down samples the network data records 126 based on a pre-determined sampling rate, such as 20 samples per second. In some implementations, the pre-determined sampling rate is set to be different for different types of data. For instance, the messaging device 102 can set a sampling rate of 60 Hz for robot motions data and a sampling rate of 5 Hz for temperature data. Other sampling rates can be set for other types of data in the robotic surgical system 110.

In another example, the messaging device 102 can analyze the network data records 126 to dynamically determine the sampling rate of the data. For instance, the messaging device 102 can analyze the changes of a certain set of data samples contained in the network data records 126 within a certain period of time, such as motion data samples of a robotic arm. If the set of data samples change smoothly from one data sample to another over the period of time, then the messing device 102 can employ a low sampling rate to reduce the size of the data samples without losing important information contained therein. If, on the other hand, the set of data samples varies dramatically from one to another, the messaging device 102 can select a high sample rate or even keep the fidelity of the original network data records 126 so that important information is not removed by the down-sampling operation.

It should be appreciated that because the messaging device 102 records substantially all the traffic data on the internal network 106, it is feasible for the messaging device 102 to down-sample the data to reduce the size and to stream the data in real time or near real time to the server device 134 for monitoring without incurring high network bandwidth consumption.

Note that in the above example, because the data trace recorder 202 captures all the network traffic on the internal network 106, the network data 122 would contain the published messages 124 captured by the message reporting service 204. Accordingly, in another example, the filtering process can identify the published messages 124 that have been recorded by the message reporting service 204 and remove those messages from the network data 122 to further reduce the size of the network data records 126.

Similar to the message reporting service 204, the data trace recorder 202 can further apply data compression mechanism as discussed above with respect to the message reporting service to compress the network data records 126 and upload the compressed network data records 126 to the server device 134 directly or indirectly. Alternatively, the data trace recorder 202 does not upload the entire network data records 126 to avoid the network bandwidth consumption caused by the uploading. Even with the filtering and compression discussed above, the network data records 126 is still much larger than the grouped messages 120. By not uploading the entire network data records 126, the network bandwidth consumption can be significantly reduced.

In addition, the data trace recorder 202 can further identify and handle sensitive data in the network data records 126 using mechanisms similar to those described above with respect to the message reporting service 204. For example, the data trace recorder 202 can identify the data fields that are considered as being sensitive and tag or label those fields. The data trace recorder 202 can also detect sensitive information by recognizing characteristic identifiers in the network data or network data records. Alternatively, or additionally, the data trace recorder 202 can employ a machine learning tool to automatically detect sensitive information. Depending on the data protection policy, the sensitive data can be removed from the network data records 126 at various stages of the process, such as before being stored in the datastore 112, before being transmitted to the relay device 116, before being transmitted to the server device, or at the server device.

Instead, the data trace recorder 202 can selectively upload network data records 126 to the server device 134. In one example, the data trace recorder 202 is configured to detect certain events and upload the network data records 126 related to the detected event. For instance, the data trace recorder 202 is configured to detect a patient injury event, based on the network data records 126 collected by the data trace recorder 202 or the grouped messages 120 recorded by the message reporting service 204. The detection is performed by the data trace recorder 202 analyzing the network data records 126 or the grouped messages 120, or by the message reporting service 204 sending a signal to the data trace recorder 202 upon detecting such an event. Upon detecting, or receiving a signal of, the event, the data trace recorder 202 identifies the network data records 126 related to such an event. The related network data records 126 can include any network traffic captured around the time when the event occurred, e.g., within thirty seconds of the detected event, or network data transmitted or received by a process or a task device where the event is detected. The data trace recorder 202 compresses and transmits the related network data records 126 out to the server device 134 as described above.

Alternatively, or additionally, the data trace recorder 202 uploads certain network data records 126 upon receiving a request. For instance, after receiving the grouped messages 120, the user 140 or a software program executing on the server device 134 determines that additional data related to the grouped messages 120 are required to perform the analysis or investigation. The server device 134 then sends a request to the messaging device 102 to retrieve the required data. The request can include one or more criteria of the retrieved data, such as the type of the requested network data records, the timestamp associated with the requested network data records, the senders or receivers of the requested network data records, and so on. Upon receiving the request, the data trace recorder 202 identifies the network data records 126 that satisfy the criteria in the request, compresses and uploads the requested network data records 126 to the server device 134. By selectively uploading the network data records 126 that are needed for the analysis, the messaging device 102 reduces the network bandwidth consumption without sacrificing the performance of the analysis.

While the above example describes selectively uploading a portion of the network data records 126 to the server device 134, it should be understood that these selected network data records 126 can be accessed and retrieved locally from the robotic surgical system 110 without uploading to the server device 134 over the external network 132. However, due to the large amount of the network data records 126 and the limited capacity of the datastore 112, the messaging device 102 maintains the network data records 126 and the grouped messages 120 in the datastore 112 only for a limited period of time, i.e. the storage time period, such as two weeks, one month or two months. In one example, the messaging device 102 implements a storage janitor or garbage collector component to clean up the datastore 112 by removing data that have exceeded the storage time period. As such, the request to retrieve the network data records 126 or the local access to the network data records 126 described above would need to be received or performed within the storage time period.

It should be understood that while the above description focuses on storing the network data records 126 and the grouped messages 120 in the datastore 112 for a limited period of time, the system can store the data in other ways. For example, the system can maintain as much data as can be stored in a fixed amount of storage. Older data can be cleared as needed, such as when the storage is running out of space. This could allow maintaining data for a longer time than the above mechanism. In another example, the system can specify different retention periods for data with different priorities. This would allow for predictable retention periods, with a longer period for higher-priority data than would be available under a scheme with uniform retention.

As can be seen from the above discussion, storing the grouped messages 120 and the network data records 126 in the datastore 112 involves storing data transmitted from multiple task devices 104. In addition to the priority of the published messages 124, the messaging device 102 organizes these network data records or messages based on the time they are generated, or transmitted. However, because of network latency, congestion, etc., it is possible that the network traffic does not arrive at the messaging device in the correct order based on the original transmit time. Further, different task devices 104 may have different internal clocks by which network data records may be timestamped, which may result in the network data records 126 or the grouped messages 120 to be stored out of order.

To address such problems, the messaging device 102 and the task devices 104 shown in FIG. 2 implement a time synchronization protocol ("TSP") 206 to synchronize the clocks on the devices throughout the internal network 106. In the robotic surgical system 110 where high precision synchronization is required, a precision time protocol ("PTP") can be implemented to achieve sub-microsecond synchronization. For example, the messaging device 102 implements a PTP master that provides sub-millisecond time synchronization with each of the task devices 104, which each implement a PTP slave. In other systems where the time precision requirement is less stringent, other types of TSP can also employed.

It should be appreciated that the data trace recorder 202 provides comprehensive recording of the information that crosses the internal network 106, including the source and destination IP address and ports. There is no need for developers, engineers or other individuals to foresee that a specific piece of information will be useful as part of an incident investigation, because substantially all the information is recorded. The data trace recorder 202 does not slow down the other parts of the robotic surgical system 110 because it is a passive listener, imposing no explicit burden on other parts of the system.

The message reporting service 204 records published messages 124 that were explicitly chosen to be recorded by engineers implementing the system. Due to the burden on system performance and on the network bandwidth, the messages to be published are chosen sparingly. One way of conserving these resources is to configure the message publishers to perform reduction of data and publish the reduced published messages 124. The data reduction can be performed based on the setting of an environment variable set by developers. For example, increased amounts of information capture in debug environments can be performed whereas reduced information in execution environments can be captured and published.

In some implementations, the robotic surgical system 110 or the messaging device 102 further determines that the current session of recording and reporting messages of the robotic surgical system 110 should be closed. For example, if the robotic surgical system 110 has reached a certain stage, such as a surgery has been completed on the robotic surgical system 110, a simulation exercise has been completed, or a set of diagnostic tests have finished, the messaging device 102 can close the current session of recording by stopping the recording and transmission of the messages. The messaging device 102 can also inform other devices regarding the closure so that proper operations can be performed. For instance, the messaging device 102 informs the relay device 116 about the closure so that the relay device 116 can delete the data related to the current session after the closure. The messaging device 102 can also inform the server device 134 to process the data one last time upon closure of the session because no additional data will be received from the messaging device 102 for the current session. The recording and transmission of messages described above will be restarted when a new session starts.

Figures 3A, 3B:
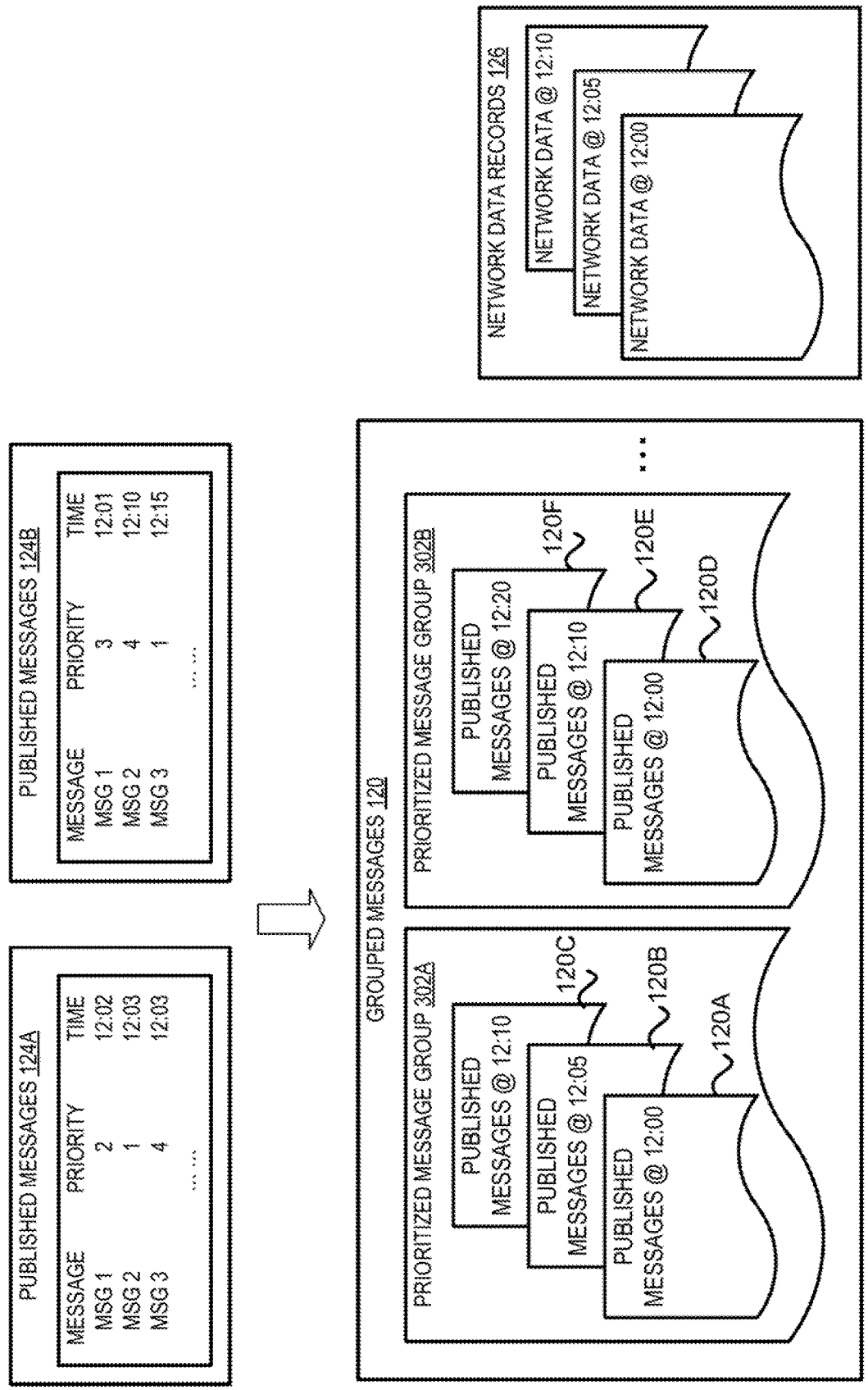
FIG. 3A shows an example of published messages and grouped messages recorded by a messaging device of the robotic surgical system.
FIG. 3B shows an example of network data records recorded by the messaging device of the robotic surgical system.

Referring now to FIG. 3A, where examples of published messages 124 and grouped messages 120 recorded by a messaging device 102 of a robotic surgical system 110 are shown. The published messages 124A and 124B might be received from different processes 218 of a task device 104 or from different task devices 104. As shown in FIG. 3A, each of the published messages 124 include the message content, such as an error message indicating a fault of the process, or a warning message showing a component of the surgical robot is at a status close to its limit. The published message 124 also includes a priority associated with the message. As discussed above, the priority can be indicated through the port from which the published messages 124 is received by the message reporting service 204 or be attached to the message itself. Likewise, the published messages 124 also includes a timestamp indicating the time when the published messages 124 is generated or transmitted by the process 128.

The message reporting service 204 records the published messages 124 received from different processes 218 or different task devices 104 and organizes the published messages 124 into grouped messages 120. In the example shown in FIG. 3A, the grouped messages 120 are organized according to the priorities of the published messages 124 and further according to the timestamps associated with the published messages 124. The message reporting service 204 first groups the published messages 124 into prioritized message groups 302A-302B. For example, prioritized message group 302A contains the published messages 124 having the highest priority, and the prioritized message group 302B contains the published messages 124 having the second highest priority. While not shown in FIG. 3A, additional prioritized message groups 302 can be established to include the published messages 124 having the third highest priority, the fourth highest priority and so on.

Within each prioritized message group 302, the message reporting service 204 further divides the published messages 124 into group messages 120A-120F. Published messages 124 in a grouped message 120 are stored and transmitted together to the server device 134. While published messages 124 are described and illustrated as being included in a grouped message 120, the grouped message 120 can include a portion of the published message 124 without including, for example, the header of the network packet contain in the published message 124, or the priority of the published messages 124.

In the example shown in FIG. 3A, the message reporting service 204 generates a grouped message 120 for every 5 minutes of published messages 124. That is, published messages 124 that are in the prioritized message group 302A and have a timestamp between 12:00 to 12:05 are included in a grouped message 120A, whereas the published messages 124 that are in the prioritized message group 302A and have a timestamp between 12:05 to 12:10 are included in a grouped message 120B. Grouped messages 120 having a higher priority are transmitted or uploaded to the server device 134 before grouped messages 120 having a lower priority. For the same priority, grouped messages 120 having earlier timestamps are transmitted or uploaded to the server device 134 before grouped messages 120 having later timestamps. As a result, grouped message 120C having a timestamp 12:10 is transmitted before the grouped message 120D having an earlier timestamp of 12:00 because the grouped message 120C has a higher priority than the grouped message 120D.

The time interval for generating the grouped messages 120 is configurable and can be the same or different for different prioritized message groups 302. In the example shown in FIG. 3A, the prioritized message group 302B has a different time interval than the prioritized message group 302A. Instead of the 5-minute interval used in the prioritized message group 302A, the prioritized message group 302B forms grouped messages 120 based on a 10-minute time interval.

By utilizing a smaller time interval for high-priority published messages 124 and a larger time interval for low-priority published messages 124, the total number of grouped messages 120 are reduced without impacting the timeliness of the high priority messages being uploaded to the server device 134. In applications where real time or near real time uploading of the published messages 124 are required, such as real-time monitoring and adjustment of the robotic surgical system 110, the time interval for generating and uploading the grouped messages 120 can be reduced to a few seconds or even sub-seconds, especially for the prioritized message group 302 having a high priority.

Further, while grouping messages may be done based on time intervals, other techniques may be used as well. For example, message groups may be sized based on a predetermined number of messages, or a total size of a group of messages. For example, a message group may be sized to be no larger than 5 megabytes, or to include no more than 25 messages. Still other techniques to group messages may be employed in some examples.

For example, messages may be grouped based on content. In one examples, multiple received messages may all relate to a single event, e.g., a failure of a surgical tool. Such messages may be grouped, even if they have different priorities, to ensure a comprehensive set of messages for a detected event is collected and transmitted together.

In a further implementation, the group messages can each be associated with an expiration date. If a group message is older than the expiration date, such as 24 hours, or one week, the group message is considered not worth transmitting and thus can be dropped.

Referring now to FIG. 3B, FIG. 3B shows an example of network data records 126 recorded by a data trace recorder 202 of a messaging device 102. Similar to the grouped messages 120, the message reporting service 204 divides the network data 122 into network data records 126 based on the timestamps associated with the network data 122. Each network data record 126 includes network data 122 that falls into a specific time interval. The example shown in FIG. 3B employs a time interval of 5 minutes. Other time intervals can also be utilized, such as a 1-minute interval or a 10-minute interval. Alternatively, other techniques may be used, such as those discussed above with respect to the published messages.

The time-based grouping or division of the grouped messages 120 and network data records 126 discussed above can be performed accurately because the clocks of the messaging device 102 and the task devices 104 of the robotic surgical system 110 have been synchronized through the TSP 206. As a result, published messages 124 and network data 122 can be correctly grouped based on their timestamps even if they are captured by the data trace recorder 202 or the message reporting service 204 out of order.

Figure 4:
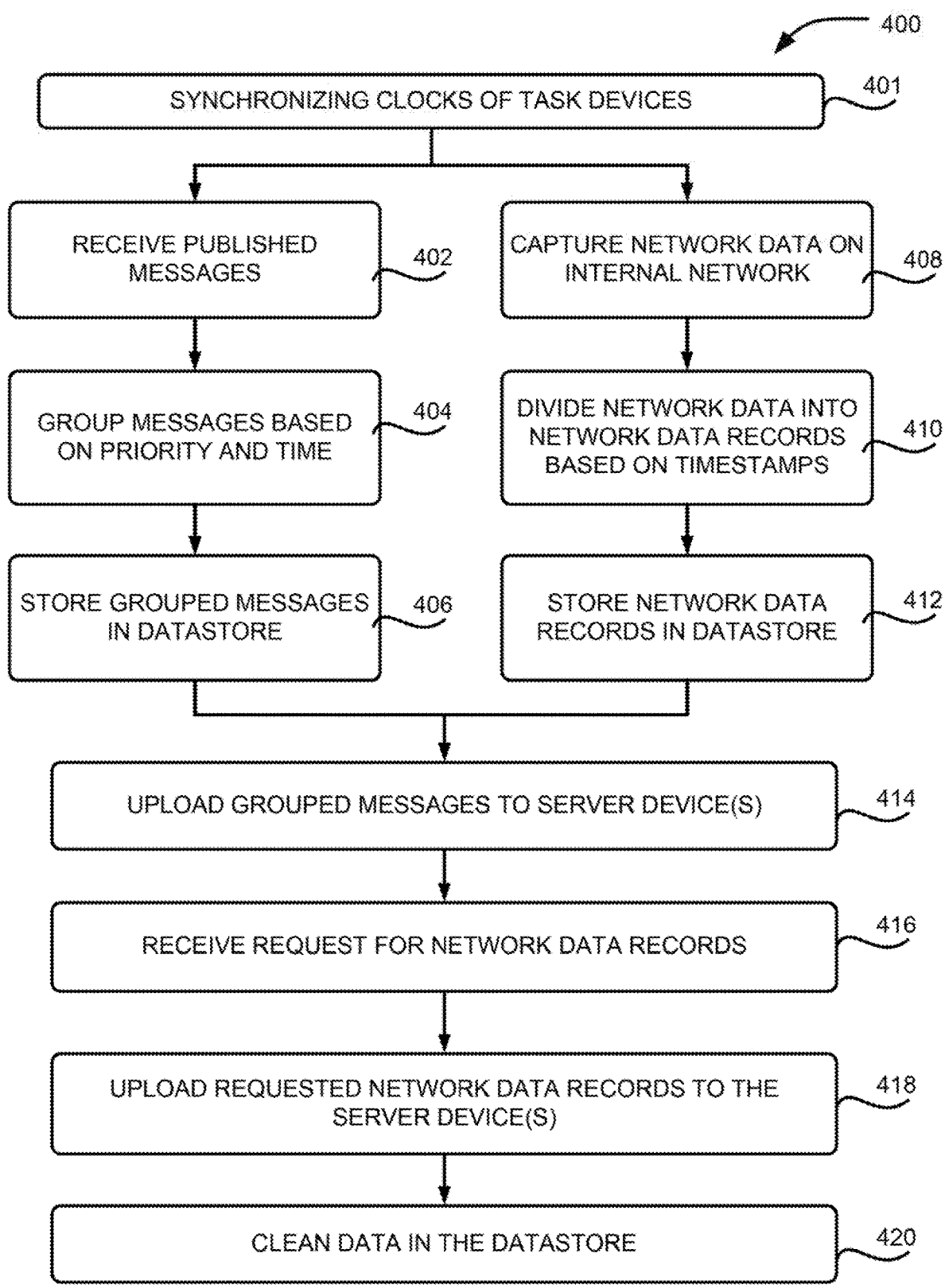
FIG. 4 shows an example of a process for comprehensively recording and reporting messages generated within a robot surgical system.

Referring now to FIG. 4, where an example of a process 400 for comprehensively recording and reporting messages generated within a robot surgical system 110 is presented. One or more computing devices (e.g., the messaging device 102) implement operations depicted in FIG. 4 by executing suitable program code (e.g., the data trace recorder 202 and the message reporting service 204). The example process 400 will be discussed with respect to the example system 100 shown in FIGS. 1 and 2, but may be employed according to any suitable system according to this disclosure.

At block 401, the process 400 involves synchronizing the clocks of the task devices 104 in the robotic surgical system 110 with the clock of the messaging device 102. In one example, the synchronization is performed via the TSP 206 implemented in the task devices 104 and the messaging device 102. At block 402, the process 400 involves receiving published messages 124 from processes 218 of task devices 104. As discussed above, a message reporting service 204 of the messaging device 102 subscribes to the processes of interest to receive the published messages 124 from those processes by listening to the respective ports of the task devices 104. Different ports might be utilized to publish messages of different priorities, and thus the priorities of the published messages 124 can be determined based on the ports where they are published. In additional or alternative implementations, the published messages 124 can each contain a priority associated therewith, or the priority may be determined based on the contents of the message, e.g., based on a mapping from a detected event, such as a patient injury, tool failure, etc. to a corresponding priority. In addition, the published messages 124 might each explicitly contain a timestamp or embedded or otherwise associated with a timestamp when published.

At block 404, the process 400 involves grouping the published messages 124 based on their priorities and timestamps to generate grouped messages 120. The message reporting service 204 of the messaging device 102 organizes the received published messages 124 into prioritized message groups 302 based on the message priorities. As a result, published messages 124 received from different processes 218 and different task devices 104 might be placed into one prioritized message group 302. The published messages 124 in each prioritized message group 302 is further divided into grouped messages 120 according to the timestamps of the published messages 124. The same or different time intervals might be used for different prioritized message groups 302. Some examples, may use other techniques, such as message size or a common event, or may use a combination of multiple techniques, e.g., time interval and a maximum grouped message size. At block 406, the process 400 involves storing the generated grouped messages 120 on a datastore 112.

At block 408, the process 400 involves capturing network data 122 on the internal network 106 of the robotic surgical system 110. The network data 122 can include all the network traffic on the internal network 106 or a portion thereof. In another implementation, the captured network data 122 does not include the published messages 124 received at block 402. At block 410, the process 400 involves dividing the network data 122 into network data records 126 based on the timestamps associated with the network data 122. For example, network data 122 generated within a 5-minute time interval is placed in one network data record 126, and network data 122 generated within a next 5-minute time interval is placed in another network data record 126. At block 412, the process 400 involves storing the network data records 126 in the datastore 112.

At block 414, the process 400 involves uploading or transmitting the grouped messages 120 to one or more server devices 134. If the robotic surgical system 110 is configured with a connection window, i.e. the robotic surgical system 110 is configured to be connectable to a network outside the internal network 106 only during the time period indicated by the connection window, the messaging device 102 uploads the grouped messages 120 to a relay device 116 through a network internal to a medical service system 130 that contain the robotic surgical system 110, such as an intranet 108 of the medical service system 130. The relay device 116 then uploads the grouped messages 120 to the server devices 134 over an external network 132 through an secure network connection. If the messaging device 102 determines to upload the network data records 126 or a portion of the network data records 126, such as upon detecting a specific event, relevant network data records 126 are also uploaded to the server device 134 at block 414 as described above. In some implementations, the data trace recorder 202 of the messaging device 102 implements a filtering process, and block 414 also involves filtering the network data 122, prior to uploading, to reduce the data size through, for example, removing certain types of network data records 126, reducing the fidelity of the network data records 126, and so on. In further implementations, the messaging device 102 is configured to detect sensitive information and to remove any sensitive information from the grouped messages 120 and the network data records 126 before uploading to the server device 134.

At block 416, the process 400 involves receiving a request to retrieve network data records 126. Such a request might be generated automatically by the server device 134 or manually by the user 140 after determining that the grouped messages 120 and any other data uploaded at block 414 are insufficient to finish the analysis or investigation. At block 418, the process 400 involves identifying and uploading the requested network data records 126 to the server device 134. Uploading the network data records 126 is performed in a way similar to block 414. At block 420, the process 400 involves cleaning the datastore 112 by removing network data records 126 and grouped messages 120 that have exceeded the storage period time so that new data can be stored in the datastore 112. The process 400 continues as more network data 122 and published messages 124 are generated in the robotic surgical system 110.

It should be understood that while the above examples focus on comprehensively recording and reporting messages in a robotic surgical system, the mechanisms described herein can be applied to any type of systems where messages are to be recorded and reported, especially those systems involving multiple devices or components communicating messages through a network. For systems that do not generate a large amount of network traffic at a high frequency as the robotic surgical system described herein, the network data records 126 can also be uploaded along with the grouped messages 120 because the network bandwidth consumption is less a concern for these systems. Further, if the size of the network data 122 is manageable, the messaging device 102 can capture the network data 122 without explicitly subscribe to and receive the published messages 124. Instead, the messaging device 102 can extract the published messages 124 from the network data 122 since the network data 122 capture substantially all the network traffic on the internal network of the system.

Figure 5:
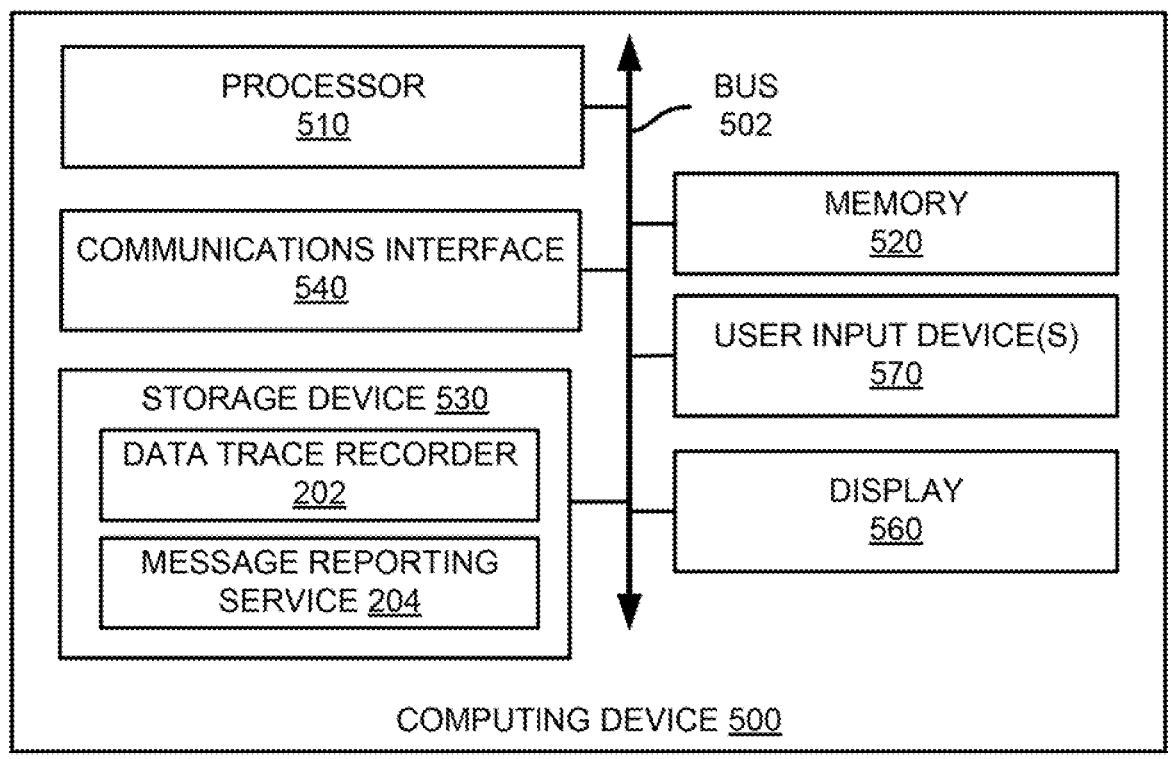
FIG. 5 shows an example of a computing device suitable for implementing aspects of the techniques and technologies presented herein.

Referring now to FIG. 5, FIG. 5 shows an example computing device 500 suitable for use in example systems or methods for comprehensively recording and reporting messages generated within a robotic surgical system. The example computing device 500 includes a processor 510 which is in communication with the memory 520 and other components of the computing device 500 using one or more communications buses 502. The processor 510 is configured to execute processor-executable instructions stored in the memory 520 to perform comprehensively recording and reporting messages generated within a robotic surgical system according to different examples, such as part or all of the example process 400 described above with respect to FIG. 4. The computing device, in this example, also includes one or more user input devices 570, such as a keyboard, mouse, touchscreen, microphone, etc., to accept user input. The computing device 500 also includes a display 560 to provide visual output to a user.

The computing device 500 can include or be connected to one or more storage devices 530 that provides non-volatile storage for the computing device 500. The storage devices 530 can store system or application programs and data utilized by the computing device 500, such as modules implementing the functionalities provided by the data trace recorder 202 and the message reporting service 204. The storage devices 530 might also store other programs and data not specifically identified herein.

The computing device 500 also includes a communications interface 540. In some examples, the communications interface 540 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as programmable logic controllers (PLCs), programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example non-transitory computer-readable storage media, that may store instructions that, when executed by the processor, can cause the processor to perform the steps described herein as carried out, or assisted, by a processor. Examples of non-transitory computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
   receiving, by a first computing device of a plurality of computing devices connected through an internal network of a surgical system, a first copy of a set of published messages based on subscriptions of the first computing device to the set of published messages, wherein the set of published messages are published by at least a second computing device of the plurality of computing devices through one or more dedicated network ports, and wherein each of the set of published messages is associated with a message priority and a timestamp generated based on a synchronized clock of the second computing device;
   capturing, by the first computing device, network data sent over the internal network of the surgical system by the plurality of computing devices, wherein the network data comprise a second copy of the set of published messages and the set of published messages is a subset of the network data, wherein the network data are associated with timestamps generated based on respective synchronized clocks of the plurality of computing devices, and wherein the respective synchronized clocks of the plurality of computing devices are synchronized based on a time synchronization protocol;
   storing, by the first computing device, the network data comprising the second copy of the set of published messages in a storage device associated with the first computing device based on the timestamps associated with the network data for a pre-determined period of time;
   storing, by the first computing device, the first copy of the set of published messages in the storage device associated with the first computing device;
   transmitting, by the first computing device over an external network, at least a portion of the set of published messages to a server device for processing according to the respective message priorities and timestamps;
   receiving, by the first computing device within the pre-determined period of time, a request to retrieve the network data, wherein the request is generated based on the portion of the set of published messages transmitted to the server device and specifies one or more criteria for retrieving the network data;
   retrieving, by the first computing device, the network data that satisfy the one or more criteria; and
   transmitting, by the first computing device over the external network, the retrieved network data to the server device in response to the request.

2. The method of claim 1, further comprising causing the surgical system to be modified based on the processing by the server device.

3. The method of claim 1, further comprising:
   filtering, by the first computing device, the network data to reduce a size of the network data prior to transmitting the retrieved network data to the server device.

4. The method of claim 1, further comprising:
   detecting, within the pre-determined period of time, a pre-defined event based on the network data;
   retrieving network data associated with the pre-defined event; and
   transmitting, by the first computing device over the external network, the network data associated with the pre-defined event to the server device.

5. The method of claim 1, wherein the first computing device of the surgical system is configured to access the external network for a pre-determined limited time period, and wherein the portion of the set of published messages are transmitted over the external network during the pre-determined limited time period.

6. The method of claim 5, wherein transmitting at least a portion of the set of published messages comprises transmitting at least a portion of the set of published messages to a relay device during the pre-determined limited time period, wherein the relay device transmits the portion of the set of published messages to the server device during or outside the pre-determined limited time period.

7. The method of claim 1, wherein transmitting at least a portion of the set of published messages comprises transmitting published messages having a highest priority without transmitting published messages having a lowest priority.

8. The method of claim 1, wherein the set of published messages further comprise published messages received from a third computing device of the surgical system, the method further comprising:
   partitioning the set of published messages according to the respective message priorities to generate at least a first group of published messages having a first priority and a second group of published messages having a second priority, the first priority being higher than the second priority, wherein at least one of the first group and the second group of published messages comprises a published message from the second computing device and a published message from the third computing device; and
   wherein transmitting at least a portion of the set of published messages comprises transmitting the first group of published messages before transmitting the second group of published messages.

9. The method of claim 8, wherein within each of the first group and the second group, a published message having an earlier timestamp is transmitted before a published message having a later timestamp.

10. The method of claim 8, further comprising generating grouped messages for the first group of published messages based on timestamps of the respective published messages in the first group, wherein the first group of published messages is transmitted by transmitting the respective grouped messages.

11. The method of claim 1, further comprising:
identifying one or more of the set of published messages as containing sensitive data; and
removing the sensitive data from the one or more of the set of published messages prior to transmitting the portion of the set of published messages.

12. The method of claim 1, further comprising:
deleting, by the first computing device, the network data from the storage device associated with the first computing device based on determining that the pre-determined period of time has passed.

13. A system comprising:
a plurality of task devices connected via an internal network, wherein one or more processes execute on the plurality of task devices, and wherein each of the plurality of task devices are configured to implement a time synchronization protocol for synchronizing clocks associated with the plurality of task devices; and
a messaging device connected with the plurality of task devices via the internal network, the messaging device comprising:
a processor; and
a non-transitory computer-readable medium having processor-executable instructions stored thereupon, which, when executed by the processor, cause the processor to:
synchronize a clock associated with the messaging device with the clocks of the plurality of task devices through implementing the time synchronization protocol;
receive a first copy of a set of published messages published by the one or more processes based on subscriptions of the messaging device to the set of published messages, each of the set of published messages associated with a message priority and a timestamp generated based on a clock of a corresponding task device;
capture network data sent over the internal network by the plurality of task devices, wherein the network data comprise a second copy of the set of published messages and the set of published messages is a subset of the network data, wherein the network data are associated with timestamps generated based on the respective clocks of the plurality of task devices;
store the network data comprising the second copy of the set of published messages in a storage device associated with the messaging device based on the timestamps associated with the network data for a pre-determined period of time;
store the first copy of the set of published messages in the storage device associated with the messaging device;
transmit, over an external network, at least a portion of the set of published messages to a server device for processing according to the respective message priorities and timestamps;
receive, within the pre-determined period of time, a request to retrieve the network data, wherein the request is generated based on the portion of the set of published messages transmitted to the server device and specifies one or more criteria for retrieving the network data;
retrieve the network data that satisfy the one or more criteria; and
transmit, over the external network, the retrieved network data to the server device in response to the request.

14. The system of claim 13, wherein the non-transitory computer-readable medium having further processor-executable instructions stored thereupon, which, when executed by the processor, cause the processor to filter the retrieved network data to reduce a size of the retrieved network data prior to transmitting the retrieved network data to the server device.

15. The system of claim 13, further comprising a relay device connected to the messaging device through a network different from the internal network,
wherein transmitting at least a portion of the set of published messages comprises:
transmitting, by the messaging device, at least the portion of the set of published messages to the relay device; and
transmitting, by the relay device, the portion of the set of published messages to the server device.

16. The system of claim 15, wherein the messaging device transmits the portion of the set of published messages to the relay device during a pre-determined limited time period when the messaging device has access to the network, and wherein the relay device transmits the portion of the set of published messages to the server device during or outside the pre-determined limited time period.

17. A computing device comprising:
a processor; and
a non-transitory computer-readable medium having processor-executable instructions stored thereupon, which, when executed by the processor, cause the processor to:
receive a first copy of a set of published messages published by at least one task device of a plurality of task devices connected through an internal network of a surgical system, wherein receiving the first copy of the set of published messages is based on subscriptions of the computing device to the set of published messages, each of the set of published messages associated with a message priority and a timestamp generated based on a clock of a corresponding task device;
capture network data sent over the internal network by the plurality of task devices, wherein the network data comprise a second copy of the set of published messages and the set of published messages is a subset of the network data, wherein the network data are associated with timestamps generated based on respective clocks of the plurality of task devices, and wherein the respective clocks of the plurality of task devices are synchronized based on a time synchronization protocol;
store the network data comprising the second copy of the set of published messages in a storage device associated with the computing device based on the timestamps associated with the network data for a pre-determined period of time;

store the first copy of the set of published messages in the storage device associated with the computing device;

transmit, over an external network, at least a portion of the set of published messages to a server device for processing according to the respective message priorities and timestamps;

receive, within the pre-determined period of time, a request to retrieve the network data, wherein the request is generated based on the portion of the set of published messages transmitted to the server device and specifies one or more criteria for retrieving the network data;

retrieve the network data that satisfy the one or more criteria; and transmit, over the external network, the retrieved network data to the server device in response to the request.

18. The computing device of claim 17, wherein the portion of the set of published messages is transmitted over the external network during a pre-determined limited time period when the surgical system is configured to access the external network.

19. The computing device of claim 18, wherein the non-transitory computer-readable medium having further processor-executable instructions stored thereupon, which, when executed by the processor, cause the processor to:

identify one or more of the set of published messages as containing sensitive data; and remove the sensitive data from the one or more of the set of published messages prior to transmitting the portion of the set of published messages to the server device.

20. A non-transitory computer-readable medium comprising processor-executable instructions to cause a processor to:

receive a first copy of a set of published messages published by at least one task device of a plurality of task devices connected through an internal network of a surgical system, wherein receiving the first copy of the set of published messages is based on subscriptions to the set of published messages, each of the set of published messages associated with a message priority and a timestamp generated based on a clock of a corresponding task device;

capture network data sent over the internal network by the plurality of task devices, wherein the network data comprise a second copy of the set of published messages and the set of published messages is a subset of the network data, wherein the network data are associated with timestamps generated based on respective clocks of the plurality of task devices, and wherein the respective clocks of the plurality of task devices are synchronized based on a time synchronization protocol;

store the network data comprising the second copy of the set of published messages in a storage device based on the timestamps associated with the network data for a pre-determined period of time;

store the first copy of the set of published messages in the storage device;

transmit, over an external network, at least a portion of the set of published messages to a server device for processing according to the respective message priorities and timestamps;

receive, within the pre-determined period of time, a request to retrieve the network data, wherein the request is generated based on the portion of the set of published messages transmitted to the server device and specifies one or more criteria for retrieving the network data;

retrieve the network data that satisfy the one or more criteria; and transmit, over the external network, the retrieved network data to the server device in response to the request.

* * * * *